United States Patent
Wager

(10) Patent No.: US 8,706,529 B2
(45) Date of Patent: Apr. 22, 2014

(54) MANAGING RELATED ELECTRONIC MEDICAL RECORDS

(75) Inventor: Douglas W. Wager, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 298 days.

(21) Appl. No.: 12/685,425

(22) Filed: Jan. 11, 2010

(65) Prior Publication Data

US 2010/0179834 A1 Jul. 15, 2010

Related U.S. Application Data

(60) Provisional application No. 61/143,596, filed on Jan. 9, 2009.

(51) Int. Cl.
*G06Q 10/00* (2012.01)
*G06Q 50/00* (2012.01)

(52) U.S. Cl.
USPC .............................................................. 705/3

(58) Field of Classification Search
USPC ......................................................... 705/2–3
See application file for complete search history.

(56) References Cited

U.S. PATENT DOCUMENTS

| | | | |
|---|---|---|---|
| 2004/0243435 A1* | 12/2004 | Williams | 705/2 |
| 2006/0117021 A1* | 6/2006 | Sidney et al. | 707/10 |
| 2007/0027720 A1* | 2/2007 | Hasan et al. | 705/3 |
| 2007/0067185 A1 | 3/2007 | Halsted | |

OTHER PUBLICATIONS

Non final OA in U.S. Appl. No. 12/685,432, mailed Feb. 29, 2012, 16 pp.
Non Final OA, mailed Aug. 15, 2012, in U.S. Appl. No. 12/685,432, 13 pp.
Final OA, mailed Feb. 27, 2013, in U.S. Appl. No. 12/685,432, 17 pp.

* cited by examiner

*Primary Examiner* — Elaine Gort
*Assistant Examiner* — Minnah Seoh
(74) *Attorney, Agent, or Firm* — Shook, Hardy & Bacon L.L.P.

(57) ABSTRACT

Systems, methods, and computer-readable media for a method for linking the health records of two or more patients and alerting them of a change in at least one of the patient's health records are provided. One method comprises, in part, receiving an indication of a desire to link the first medical record of the first patient to a second medical record of a second patient and searching a connected health network for at least one of the first medical record associated with the first patient or the second medical record associated with the second patient. The method further comprises designating a sharing level between the first medical record of the first patient and the second medical record of the second patient, the sharing level indicating an extent of healthcare information that can be shared between the first medical record and the second medical record. The method also includes requesting the second patient to accept a link between the first medical record and the second medical record, and linking the first medical record associated with the first patient and the second medical record associated with the second patient.

17 Claims, 5 Drawing Sheets

CONNECTED HEALTH NETWORK ALERTS FOR PATIENT 1

| ALERT TYPE | RISK | RELATIONSHIP | ALERT | STATUS |
|---|---|---|---|---|
| ALLERGY | HIGH | CHILD | PENICILLIN ALLERGY: SEVERE | ACTIVE |
| GENETIC | HIGH | SPOUSE | MARKER FOR CF | ACTIVE |
| HEREDITARY RISK | LOW | SIBLING | DIAGNOSIS: BREAST CANCER TYPE XYZ DIAGNOSED 9.12.2005 | ACTIVE |
| INFECTIOUS DISEASE | MODERATE | SPOUSE | DIAGNOSIS: HPV | ACTIVE |
| ALLERGY | LOW | FREQUENT CONTACT | PENICILLIN ALLERGY: MODERATE | INACTIVE |

FIG. 4.

MANAGING RELATED ELECTRONIC MEDICAL RECORDS

CROSS-REFERENCE TO RELATED APPLICATIONS

This application claims the benefit of U.S. Provisional Patent Application No. 61/143,596, filed Jan. 9, 2009, entitled "Formation of Relationships Among Multiple Electronic Health Records," which is incorporated by reference herein. This application is related by subject matter to U.S. patent application Ser. No. 12/685,432 filed even date herewith and entitled "Alerts Based On Related Electronic Health Records", which is assigned or under obligation of assignment to the same entity as this application, and incorporated in this application by reference.

SUMMARY

Within a health care system, proactive health management may be achieved by allowing patients, based on relationships and contact, to connect or link medical records for cross-record alerting. Such a connection would allow one, using rules and alerts, to search across records for specified conditions. For example, if a wife had a marker for Cystic Fibrosis, an alert may be provided to the husband to suggest testing the husband for the marker, before they have children. Linking medical records may also be used for drug/condition interaction alerts. For example, if a husband is using a drug that is harmful to pregnant women when in contact (e.g., Propetia), his wife becomes pregnant, and this condition is recorded in her health record, the husband would be alerted to the risks of using such a drug.

In one embodiment of the present invention, a computer-implemented method for linking two or more medical records is provided, where a first patient has a medical record. The method comprises, in part, receiving an indication of a desire to link the first medical record of the first patient to a second medical record of a second patient and searching a connected health network for at least one of the first medical record associated with the first patient or the second medical record associated with the second patient. The method further comprises designating a sharing level between the first medical record of the first patient and the second medical record of the second patient, the sharing level indicating an extent of healthcare information that can be shared between the first medical record and the second medical record. The method also includes requesting the second patient to accept a link between the first medical record and the second medical record, and linking the first medical record associated with the first patient and the second medical record associated with the second patient.

BRIEF DESCRIPTION OF THE DRAWINGS

Embodiments are described in detail below with reference to the attached drawing figures, wherein:

FIG. 4 is an illustrative graphical user interface display of a connected health network alert for a patient in accordance with embodiments of the present invention.

DETAILED DESCRIPTION

Figure 1:
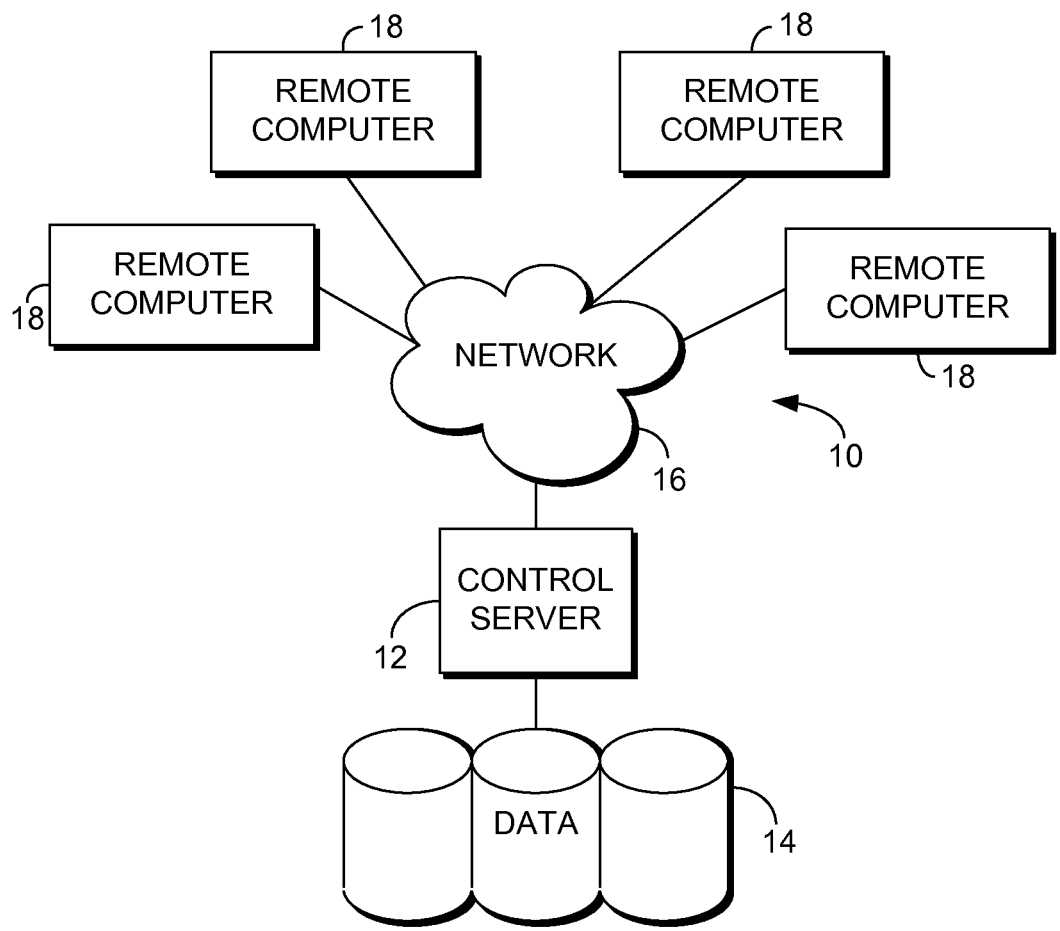
FIG. 1 is a block diagram of an exemplary computing environment suitable for use in implementing embodiments of the present invention.

With reference to FIG. 1, an exemplary medical information system 10 for implementing embodiments of the invention includes a general purpose-computing device in the form of control server 12. Components of control server 12 may include, but are not limited to, a processing unit, internal system memory, and a suitable system bus for coupling various system components, including database cluster 14 to the control server 12. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 12 typically includes therein or has access to a variety of computer readable media, for instance, database cluster 14. Computer readable media can be any available media that can be accessed by server 12, and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 12. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 14, discussed above and illustrated in FIG. 1, provide storage of computer readable instructions, data structures, program modules, and other data for server 12. Server 12 may operate in a computer network 16 using logical connections to one or more remote computers 18. Remote computers 18 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians and caregivers include, but are not limited to, the treating physician, specialists such as surgeons, radiologists and cardiologists, emergency medical technologists, discharge planners, care planners, physician's assistants, nurse practitioners, nurses, nurse's aides, pharmacists, dieticians, veterinarians and the like. The remote computers 18 may also be physically located in nontraditional medical care environments so that the entire health care community is capable of integration on the network. Remote computers 18 may be a personal computer, server, router, a network PC, a peer device, other common network node or the like, and may include some or all of the elements described above relative to server 12. Computer network 16 may be a local area network (LAN) and/or a wide area network (WAN), but may also include other networks. Such networking environments are commonplace in offices, enterprise-wide computer networks, intranets and the Internet. When utilized in a WAN networking environment, server 12 may include a modem or other means for establishing communications over the WAN, such as the Internet. In a networked environment, program modules or portions thereof may be stored in server 12, or database cluster 14, or on any of the remote computers 18. For example, and not limitation, various application programs may reside on the memory associated with any one or all of remote computers 18. It will be appreciated that the network connections shown are exemplary and other means of establishing a communications link between the computers may be used.

A user may enter commands and information into server 12 or convey the commands and information to the server 12 via remote computers 18 through input devices, such as keyboards, pointing devices, commonly referred to as a mouse, trackball, or touch pad. Other input devices may include a microphone, scanner, or the like. Server 12 and/or remote computers 18 may have any sort of display device, for instance, a monitor. In addition to a monitor, server 12 and/or computers 18 may also include other peripheral output devices, such as speakers and printers.

Although many other internal components of server 12 and computers 18 are not shown, those of ordinary skill in the art will appreciate that such components and their interconnection are well known. Accordingly, additional details concerning the internal construction of server 12 and computer 18 need not be disclosed in connection with the present invention. Although the method and system are described as being implemented in a LAN operating system, one skilled in the art would recognize that the method and system can be implemented in any system.

Figure 2:
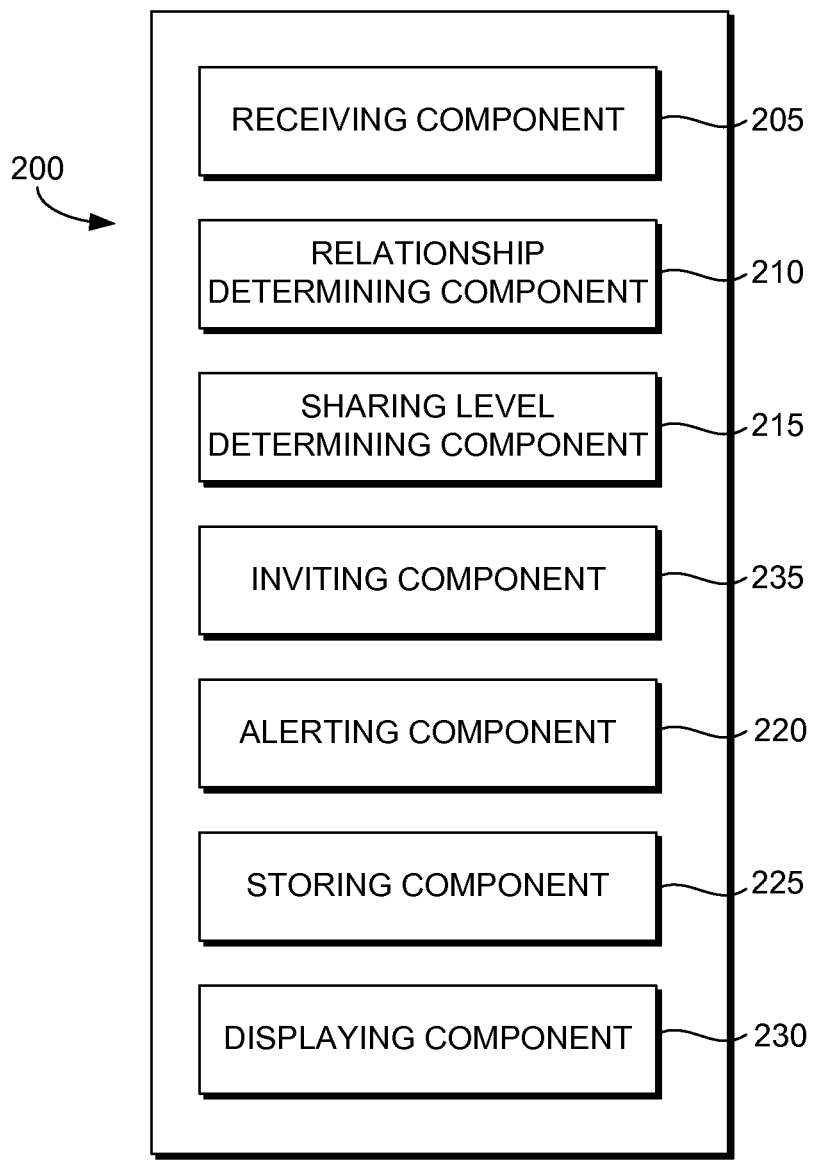
FIG. 2 is an exemplary computer system for linking health records and alerting patients within a connected health network in accordance with an embodiment of the present invention.

As previously set forth, embodiments of the present invention relate to computing systems for linking two or more patients' health records. With reference to FIG. 2, a block diagram is illustrated that shows exemplary computing system architecture configured for linking patients' health records and alerting one patient of changes in the other patient's health record in accordance with an embodiment of the present invention. It will be understood and appreciated by those of ordinary skill in the art that the computing system architecture shown in FIG. 2 is merely an example of one suitable computing system and is not intended to suggest any limitation as to the scope of use or functionality of the present invention. Neither should the computing system architecture be interpreted as having any dependency or requirement related to any single module/component or combination of modules/components.

The computing system includes a health record linking and alerting module 200. Health record linking and alerting module 200 creates a link between two or more members of a connected health network based on a specified relationship level between the members, such as spouse, sibling, parent/child, etc. Health record linking and alerting module 200 further alerts each member if a condition is added or changed in another member's record that, based on the relationship or sharing level between the members, should be known to that member. The module 200 displays the alerts, including health related actions that may need to be taken based on the alert. The module 200 allows a caregiver to raise the level of care from managing individual patients or members in view of other patients related to or in contact with that member.

Health record linking and alerting module 200 allows a user to create an association between a health record for a patient and a health record for one or more other patients to establish a link that may be used for alerting the associated patients. The health record linking and alerting module 200 is configured for alerting a patient of an issue with another patient if it may affect the initial patient. Health record linking and alerting module 200 may reside on one or more computing devices, such as, for example, computing device 100 described above with reference to FIG. 1. By way of example only and not limitation, computing devices may be a server, personal computer, desktop computer, laptop computer, handheld device, mobile handset, consumer electronic device, or the like. It should be noted, however, that embodiments are not limited to implementation on such computing devices, but may be implemented on any a variety of different types of computing devices within the scope of embodiments thereof.

Health record linking and alerting module 200 comprises receiving component 205, relationship determining component 210, sharing level determining component 215, inviting component 235, alerting component 220, storing component 225, and displaying component 230. Receiving component 205 receives or accesses health records for a patient, particularly a patient within a connected health network. By way of example, a health care professional, such as a physician, may electronically access a health record for a patient upon admission to the current care venue or later upon learning of the information while the patient is being treated at the current care venue. A health record may also be gathered and entered manually. In another embodiment, the health records may be electronically transferred to the module 200.

Relationship determining component 210 determines the relationship level between two or more patients when linking the health records of the patients within a connected health network. Examples of relationship levels include any familial relationship (e.g., spouses, siblings, father/child, extended families), co-inhabitant, etc. Each relationship level provides a different concern when linking and alerting health records. Exemplary concerns when patients have a familial relationship include checking for hereditary diseases, drug interaction risks between spouses, etc. For example, spouses may be connected in order to identify whether, as a couple, they are at risk of having children with hereditary diseases, such as cystic fibrosis. Parent/children may be linked to suggest testing or interventions for children if a genetically-transferred disease is identified in the parent.

In a co-inhabitant relationship, the patients may not be directly related, but may reside in the same location or otherwise be in close proximity to each other. In such a situation, health concerns that may be addressed proactively using linked health records include, for example, allergies to drugs, diseases spread through shared living areas, etc.

In one embodiment, the relationship determining component 210 receives a specified relationship level from one or more of the patients directly. For example, when a first patient wishes to have their health record linked to a second patient, the patients (directly or through care providers) may, at that time, designate their relationship with the second patient. If one of the patients does not specify the relationship level between the linked patients, the relationship determining component 210 may request a patient to designate a relationship level. In further embodiments, the relationship determining component 210 may determine a relationship level between two patients without input from either patient. For example, when a mother gives birth to a child and the child's health record is originated, the relationship level between the mother and child is automatically determined.

The sharing level determining component 215 is configured to determine a sharing level between patients or members within a connected health network. Examples of sharing levels include spouse, sibling, parent/child, and frequent contact. For a frequent contact level, information that may be shared and alerted includes information that could directly affect either patient based on allergies or diseases spread commonly through shared living areas. For a spouse sharing level, the rules of a frequent contact level would apply, as well as cross-checking information on genetic markers for specific diseases (e.g., Cystic Fibrosis) and other diseases that may be more prevalent if both parents are carriers. Alerts for mental health and sexually transmitted diseases are optional for confidentiality reasons, and access and availability dependent upon the consent of the patient. A sibling sharing level may share and alert information to another patient for diseases that tend to follow family lines, but are not yet indicated by genetic markers. It is also dependent on the gender of the patient. For example, a sister that develops breast cancer at a young age may cause an alert with the other sister, even though a genetic marker may not be indicated. Also, a brother in the family would not be alerted based on gender and the relative likelihood of breast cancer. For a parent/child sharing level, the information shared and alerted follows similar rules as for sibling sharing level, but adjusted for parental relationship and gender. It may further include rules regarding sexually transmitted diseases if the disease was diagnosed prior to birth of the child patient.

Inviting component 235 is configured to invite patients to join a connected health record network. In embodiments, the inviting component 235 may be used when one patient wishes to be linked or connected to another patient, via their health records. For example, the first patient may invite the second patient to join the connected health record network in order to provide an opportunity to link health records.

Alerting component 220 is configured to alert patients that are linked to another patient, via health records, when one of the patient's health records changes. For example, if patient A and patient B have connected health care records, and patient B's health changes, thus causing a change in his medical record, patient A may be automatically alerted of this change if it is determined that the specific change to patient B's health record may have an effect upon patient 1.

Storing component 220 is configured for storing information associated with health records for a patient. In various embodiments, such information may include, without limitation, current and previous treatments for a patient; current medications; allergies; genetic records; relationships between other patients, etc.

An exemplary storing component is depicted by data store 14 of FIG. 1. In embodiments, the storing component 225 is configured to be searchable for one or more of the items stored in association therewith. It will be appreciated by those of ordinary skill in the art that the information stored in the storing component 225 may be configurable and may include a variety of information relevant to patient's health records. Further, though illustrated as a single, independent component, the storing component 225 may, in fact, be a plurality of storage devices, for instance a database cluster, portions of which may reside on the server 12 of FIG. 1, one or more end user devices 18, another external computing device (not shown), and/or any combination thereof.

Displaying component 225 is configured for electronically displaying health records of patients. Displaying component 225 also is configured for displaying alerts for patients (e.g., as discussed with respect to FIG. 4).

Figure 3:
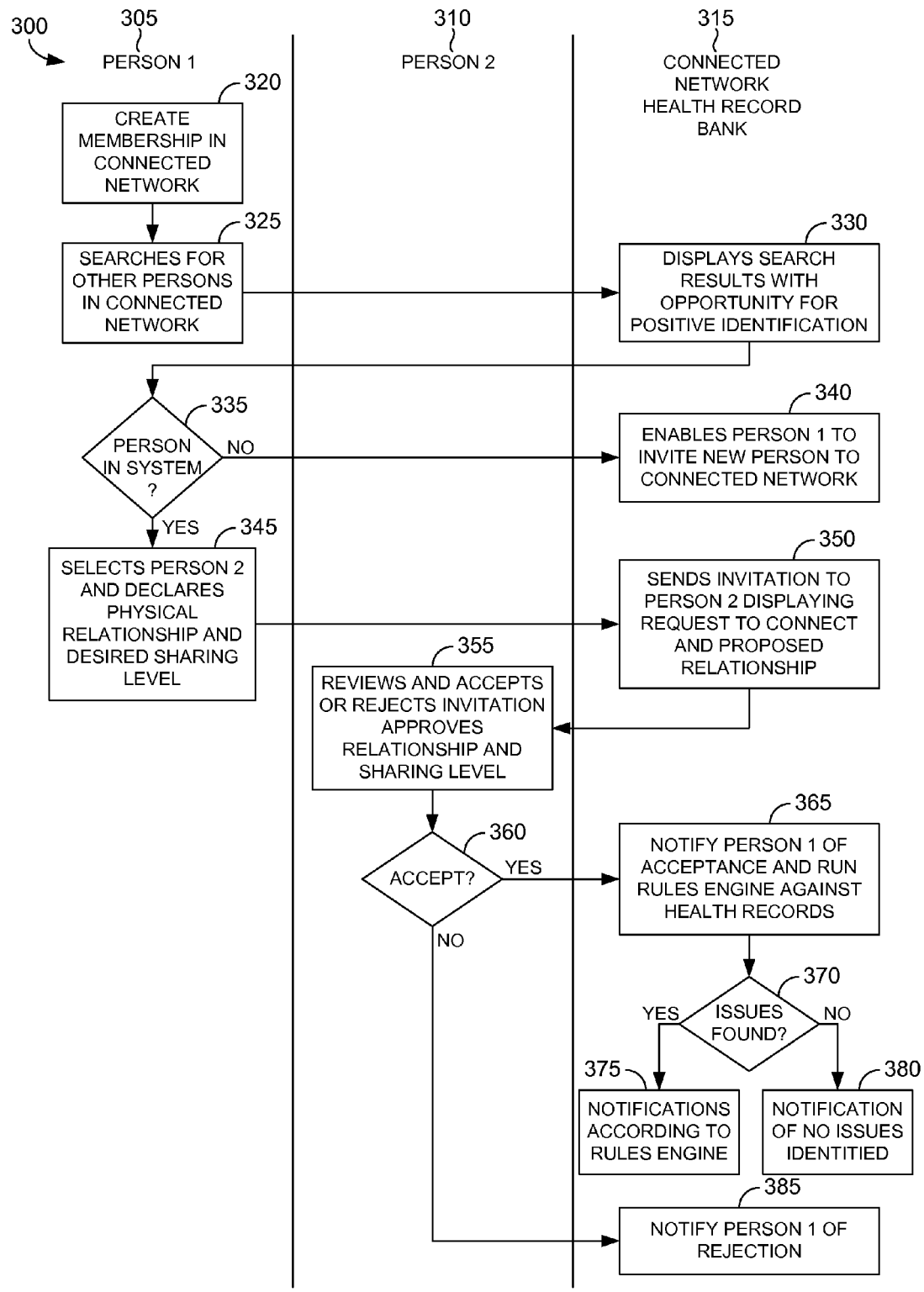
FIG. 3 is a flow diagram illustrating a method for linking health records of patients within a connected health network in accordance with an embodiment of the present invention.

Referring next to FIG. 3, a method 300 is provided for creating connections between (and among) multiple patients. As illustrated in FIG. 3, three levels are shown: a person 1 (305), a person 2 (310), and a connected network health record bank 315 ("connected network"). The connected network 315 provides a general system of health records for patients, which may be stored, for example, in storing component 225 of FIG. 2.

Initially, as indicated at block 320, patient 1 creates a membership in the connected network 315. Creating a membership may include providing a health record for storage on the connected network. Such a health record may be provided in electronic form, or alternatively, an electronic health record may be created for person 1 once the connected network has received person 1's health record. After person 1 has created a membership in the connected network, person 1 may then search for other persons (such as person 2) within the network, as indicated at block 325. Typically, person 1 may search for other persons to which person 1 has a relationship (e.g., familial relationship) or otherwise desires to connect health records. At block 330, the search results of person 1's query are displayed, where the results are received from the connected network (e.g., in data store 14 in FIG. 1). At block 335, person 1 views the displayed search results and determines whether the person who they are searching for is in the network. For illustrative purposes, in FIG. 3, person 1 is searching for person 2. If person 2 is not displayed in the search results, person 1 is enabled to invite person 2 to join the connected network, as indicated at block 340.

If person 2 is a member of the connected network, as determined at block 335, person 1 selects person 2 and declares the physical relationship and desired sharing level. This is indicated at block 345. Upon selecting person 2, at block 350, an invitation is sent to person 2 displaying a request to connect with person 2's health record, along with displaying the proposed relationship and sharing level. After receiving the invitation, person 2, at block 355, reviews and accepts or rejects the invitation. Person 2, at this time, may also accept or reject the proposed relationship and sharing level proposed by person 1. In embodiments, person 2 may suggest or propose another relationship and/or sharing level than what was originally proposed by person 1. If at block 360, person 2 accepts, person 1 is then notified of the acceptance at block 365. If instead, at block 360, person 2 rejects the invitation, person 1 is notified of the rejection at block 385. Further, at block 365, a rules engine is applied to the data in the health records of both person 1 and person 2 (e.g., where the rules engine resides on server 12 of FIG. 1). The rules engine may search for any conditions, medication, allergies, genetic markers, etc. in each person's record that, based on the relationship and sharing levels between the persons, may affect the other person's health. As discussed above, the rules engine also may take into account confidentiality and access issues related to certain issues, where even if an issue was found (e.g., at block 370), the other person would not be notified. If the rules engine does find an issue and does determine that the other person should be notified, this occurs at block 375. If no issues are found, both person 1 and person 2 are notified that no issues were identified at block 380.

With reference to FIG. 4, an illustrative screen display 400 is shown. In accordance with an embodiment of the present invention, generally, exemplary user interface 400 comprises a connected health network alert area ("alert area") 430. The connected health network alert area 430 may be displayed anywhere within the graphic user interface.

The alert area 430 displays the alerts for patient 1 determined by the connected health network and its rules engine. One skilled in the art will appreciate that the alert area 430 may be displayed in any location viewable by the patient's health care professional. Exemplary locations include patient 1's electronic health record, or in a secured web site that lists patient 1's risk factors with the relationship expressed. It will be understood that if alerts were displayed using such a web site, no identifiable data would be displayed.

The screen display 400 provides a view of a patient's alerts that are displayed as a result of a change in another patient's health record, where the other patients are linked to the displayed patient's health record. As discussed above, the alerts relate to diseases, conditions, drug allergies, genetic markers, medications, etc.

In the illustrated example, various categories are displayed, such as alert type 405, risk 410, relationship 415, alert 420, and status 425. These categories may vary based on the patient and/or health care setting, and further may be tailored based on the specific patient. In addition, the alert area 430 and categories may be personalized for all patients within a connected group.

Alert type 405 designates the type of alert provided to patient 1. By way of example, without limitation, alert types can include allergy, genetic, hereditary risk, infectious disease, medication, etc. Risk category 410 displays the risk level of the alert to the health of patient 1. The risk level for each patient will vary based on the general health of the patient, specific health conditions the patient may have, the relationship between a second patient and the patient 1, the specific alert, and the status of the alert. Further, the patient or his health care professional may customize the rules engine to classify the risk level of a certain alert.

The relationship 415 designates the relationship level between patient 1 and the patients whose alerts are displayed. For example, the first listed alert, which relates to a patient with an allergy of penicillin, is associated with a child of patient 1. One skilled in the art will appreciate that the sharing level of the alert may also be displayed either with the relationship level or in place of the relationship level.

The specific alert is shown in the column referenced at 420. Here, the alert 420 lists the specific disease, condition, allergy, etc. that may be relevant to patient 1. As is illustrated, the alert may vary in specificity and detail. For example, one alert lists only a diagnosis of HPV, while another alert lists a diagnosis of breast cancer, along with the type of breast cancer, and diagnosis date. In another example, two alerts are listed that correspond with a penicillin allergy, but one is listed as severe, while the other is listed as moderate. These alerts also illustrate the relationship that can exist between the alert and the risk level, where the severe allergy is given a high risk level and the moderate allergy is given a low risk level. Further, one skilled in the art will appreciate that the alerts may be grouped or listed in any manner necessary. For example, the alerts may be listed in order of risk, relationship, or type.

The status 425 of the alert is also displayed in the alert area 430 of FIG. 4. Having a status list 425 allows for the health care professional to note when an alert may no longer be active.

Figure 5:
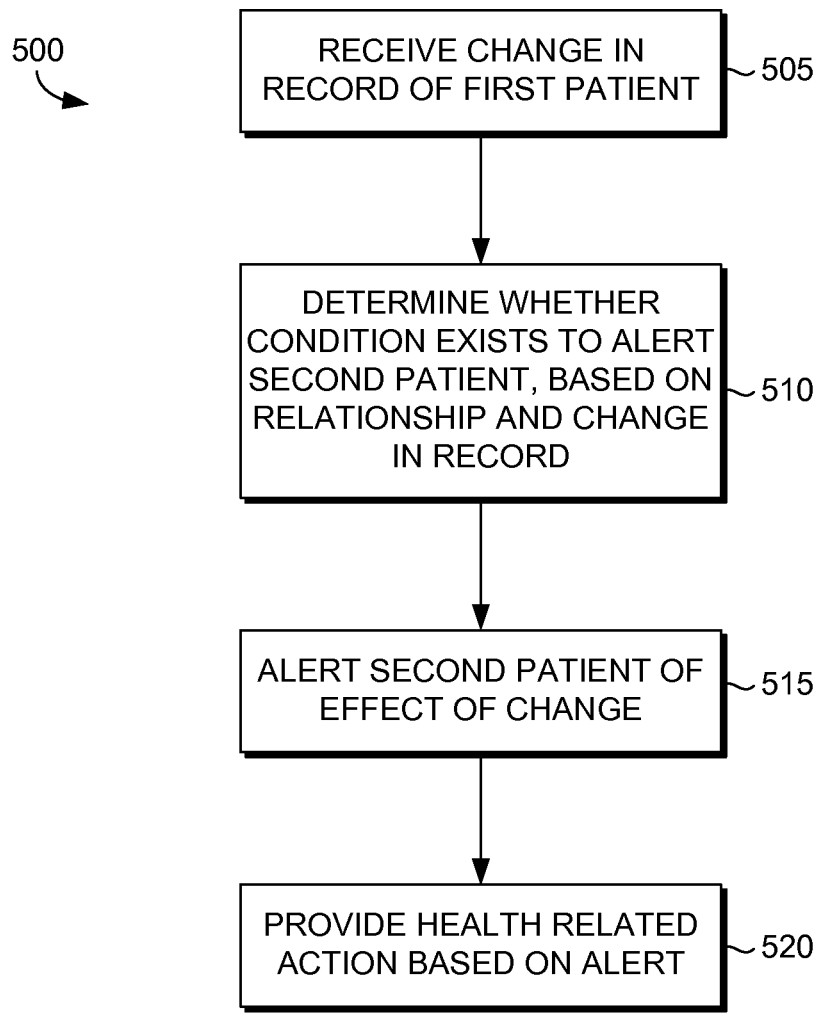
FIG. 5 is a flow diagram illustrating a method for alerting patients within a connected health network in accordance with embodiments of the present invention.

Referring next to FIG. 5, a method 500 is provided for alerting linked patients of a change in another patient's health record that may affect their own health. More specifically, method 500 occurs after the health records of the two patients are linked, as described above. Once the health records are linked within a connected health network, alerts may be sent or displayed from one patient's record to the other.

Initially, as indicated at block 505, information in the health record of a first patient is added to, changed, or deleted. Such information may be received, for example, by input of any health care professional, such as a physician. One skilled in the art will appreciate that any addition or change may be received at block 505. Once a change is received, a rules engine will determine whether a condition exists that would necessitate a second patient to receive an alert, where the first and second patients are linked via their health records. This is indicated at block 510. Determining a condition may occur in any number of ways. By way of example, without limitation, a rules engine bases the determination on the type of information that has changed, along with the relationship or sharing level between the first and second patients. Such a determination may be altered based on the needs of the second patient, the desired confidentiality of the first patient, and the opinion of either patient's health care professional.

Next, at block 515, the second patient is alerted of the effect of the change. The second patient may also be alerted of the information changed. An alert may take any form known in the art, such as by being displayed using displaying component 230 of FIG. 2. At block 520, a health related action based on the determined alert may be provided to the patient. For example, if a genetic marker is detected in the first patient, and the relationship level between the first and second patient is parent/child, the second patient may be genetically tested for the genetic marker.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of the invention. A skilled programmer may develop means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. A computer-implemented method for linking two or more medical records, wherein a first patient has a first medical record, the method comprising:

receiving an indication of a desire to link the first medical record of the first patient to a second medical record of a second patient;

searching a connected health network for at least one of the first medical record associated with the first patient or the second medical record associated with the second patient;

automatically selecting a sharing level from among a plurality of sharing levels based on a type of relationship between the first patient and the second patient, wherein each of the sharing levels indicates an extent of healthcare information that can be shared between the first medical record and the second medical record in accordance with a unique set of health concerns associated with the type of relationship between the first patient and the second patient;

requesting the second patient to accept a link between the first medical record and the second medical record;

linking the first medical record associated with the first patient and the second medical record associated with the second patient;

in accordance with the sharing level, automatically searching, via a computing device, the second medical record associated with the second patient for any conditions, medications, allergies, or genetic markers that may affect the health of the first patient; and in response to identifying at least one condition, medication, allergy, or genetic marker that may affect the health of the first patient, automatically alerting the first patient that a potential health risk exists in association with the first patient.

2. The method of claim 1, further comprising:
determining the sharing level between the first medical record and the second medical record.

3. The method of claim 2, wherein the sharing level comprises a spousal sharing level, a sibling sharing level, a frequent-contact sharing level, or a parent/child sharing level.

4. The method of claim 1, further comprising:
recognizing a relationship level between the first patient and the second patient.

5. The method of claim 4, wherein the relationship level comprises a spousal relationship level, a child/parent relationship level, a sibling relationship level, or a co-inhabitant relationship level.

6. The method of claim 4, wherein the sharing level is designated based on the relationship level between the first patient and the second patient.

7. The method of claim 1, further comprising:
alerting the first patient of a change in the second medical record of the second patient.

8. The method of claim 1, further comprising:
alerting the second patient of a change in the first medical record of the first patient.

9. The method of claim 1, further comprising:
in accordance with the designated sharing level, alerting the first patient of any medical conditions, medications, allergies, or genetic markers of the second patient that may affect the first patient.

10. The method of claim 1, further comprising:
in accordance with the designated sharing level, alerting the second patient of any medical conditions, medications, allergies, or genetic markers of the first patient that affect may the second patient.

11. The method of claim 1, wherein the first patient indicates the desire to link the first medical record of the first patient to the second medical record of a second patient.

12. The method of claim 1, wherein the first patient indicates the sharing level between the first medical record of the first patient and the second medical record of the second patient.

13. The method of claim 1, wherein the request to the second patient to accept a link between the first medical record and the second medical record includes the designated sharing level.

14. One or more computer-storage devices having computer executable instructions embodied thereon that, when executed, perform a method for relating two or more electronic medical records within a connected health network having a plurality of electronic medical records, the method comprising:

identifying a relationship level from among a plurality of relationship levels with each of the relationship levels being associated with a unique set of health concerns, the relationship level indicating an extent of the relationship between a first patient and a second patient, wherein the first patient is associated with a first electronic medical record and the second patient is associated with a second electronic medical record within a connected health network;

based on an existence of a relationship between the first patient and the second patient, linking the first electronic medical record associated with the first patient and the second electronic medical record associated with the second patient so that healthcare information associated with the first patient is shared between the first electronic medical record and the second electronic medical record;

in accordance with the relationship level between the first patient and the second patient, the unique set of health concerns, and the gender of the second patient, determining that at least one of a condition, a medication, an allergy, or a genetic marker associated with the first patient may affect health of the second patient; and in response to determining that the at least one of the condition, the medication, the allergy, or the genetic marker associated with the first patient may affect the health of the second patient, automatically providing an alert for the second patient to indicate that a potential health risk exists in association with the second patient.

15. The device of claim 14, wherein an extent of the healthcare information is shared in accordance with the type of the relationship between the first patient and the second patient.

16. The device of claim 14, wherein the type of relationship between the first patient and the second patient comprises a spousal relationship type, a child/parent relationship type, a sibling relationship type, or a co-inhabitant relationship type.

17. One or more computer-storage devices having computer executable instructions embodied thereon that, when executed, perform a method for relating two or more electronic medical records within a connected health network having a plurality of electronic medical records, the method comprising:

recognizing an indication that a relationship exists between a first patient and a second patient, the first patient being associated with a first electronic medical record and the second patient being associated with a second electronic medical record linked to the first electronic medical record within the connected health network;

in accordance with the indication that the relationship exists between the first patient and the second patient, accessing the second electronic medical record to identify at least one of a condition, a medication, an allergy, or a genetic marker associated with the second patient that may affect health of the first patient based on the relationship between the first patient and the second patient;

providing an indication of the at least one of the condition, the medication, the allergy, or the genetic marker associated with the second patient that may affect the health of the first patient, the indication being provided within the first electronic medical record associated with the first patient; and based on the identification of the at least one of the condition, the medication, the allergy, or the genetic marker associated with the second patient that may affect the health of the first patient, automatically providing an alert for the first patient to indicate that a potential health risk exists in association with the first patient.

* * * * *